United States Patent [19]

Mittermeier et al.

[11] Patent Number: 5,250,559
[45] Date of Patent: Oct. 5, 1993

[54] MICROBICIDAL COMPOSITIONS

[75] Inventors: Ludwig Mittermeier, Freiburg, Fed. Rep. of Germany; Wilhelm Ruess, Pfeffingen, Switzerland

[73] Assignee: Ciba-Geigy Corporation, Ardsley, N.Y.

[21] Appl. No.: 920,023

[22] Filed: Jul. 27, 1992

Related U.S. Application Data

[63] Continuation of Ser. No. 826,187, Jan. 21, 1992, abandoned, which is a continuation of Ser. No. 649,130, Jan. 29, 1991, abandoned, which is a continuation of Ser. No. 435,920, Nov. 13, 1989, abandoned.

[30] Foreign Application Priority Data

Nov. 18, 1988 [CH] Switzerland .......................... 4284/88

[51] Int. Cl.$^5$ ............................................. A01N 43/64
[52] U.S. Cl. .................................................... 514/383
[58] Field of Search ........................................ 514/383

[56] References Cited

FOREIGN PATENT DOCUMENTS 1522657 8/1978 United Kingdom .
2098607 11/1982 United Kingdom .

*Primary Examiner*—Allen J. Robinson
*Attorney, Agent, or Firm*—Edward McC. Roberts

[57] ABSTRACT

The combination of the plant microbicide 1-[2-(2,4-dichlorophenyl)-4-propyl-1,3-dioxolan-2-ylmethyl]-1H-1,2,4-triazole (=propiconazole) with the plant microbicide 1-{2-[2-chloro-4-(4-chlorophenoxy)-phenyl]-4-methyl-1,3-dioxolan-2-ylmethyl}-1H-1,2,4-triazole results in an increased activity in the control of plant diseases. Plant microbicidal compositions based on such combinations are suitable especially for controlling diseases in cereals.

9 Claims, No Drawings

MICROBICIDAL COMPOSITIONS

This application is a continuation of application Ser. No. 07/826,187, filed Jan. 21, 1992, now abandoned, which is a continuation of application Ser. No. 07/649,130, filed Jan. 29, 1991, now abandoned, which is a continuation of application Ser. No. 07/435,920, filed Nov. 13, 1989, now abandoned.

The present invention relates to microbicidal mixtures having a synergistically increased activity against plant diseases and to methods for the use of such mixtures, especially in cereals.

The invention relates especially to the control and prevention of diseases in cereal cultivation.

A mixture that has proved unexpectedly favourable is a combination of the active ingredient component I), 1-[2-(2,4-dichlorophenyl)-4-propyl-1,3-dioxolan-2-ylmethyl]-1H-1,2,4-triazole (=propiconazole) of formula I

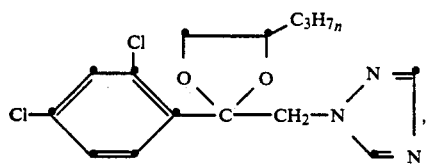

or a salt thereof, with the active ingredient component II), 1-{2-[2-chloro-4-(4-chlorophenoxy)-phenyl]-4-methyl-1,3-dioxolan-2-ylmethyl}-1H-1,2,4-triazole of formula II

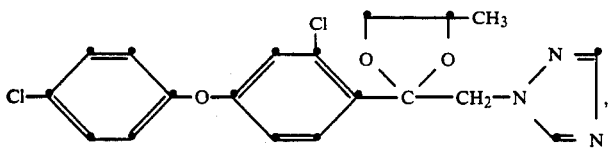

or a salt thereof.

The compound of formula I is described in GB 1 522 657.

The compound of formula II is described as a fungicidal active substance in GB Patent Application No. 2 098 607. The activity of these two triazole derivatives is founded especially on the inhibition of ergosterol biosynthesis in the development cycle of phytopathogenic fungi.

The mentioned salts of compounds I and II can be prepared by reacting the respective base with acids.

Of the acids that are suitable, the following may be mentioned: hydrohalic acids, such as hydrofluoric acid, hydrochloric acid, hydrobromic acid or hydriodic acid, as well as sulfuric acid, phosphoric acid, nitric acid and organic acids, such as acetic acid, trifluoroacetic acid, trichloroacetic acid, propionic acid, glycolic acid, thiocyanic acid, lactic acid, succinic acid, citric acid, benzoic acid, cinnamic acid, oxalic acid, formic acid, benzenesulfonic acid, p-toluenesulfonic acid, methanesulfonic acid, salicylic acid, p-aminosalicylic acid, 2-phenoxybenzoic acid, 2-acetoxybenzoic acid or 1,2-naphthalenedisulfonic acid.

The term "salts" also includes metal complexes of the basic components I or II. These complexes consist of the fundamental organic molecule and an inorganic or organic metal salt, for example the halides, nitrates, sulfates, phosphates, acetates, trifluoroacetates, trichloroacetates, propionates, tartrates, sulfonates, salicylates, benzoates etc. of elements of the second main group, such as calcium and magnesium, and of the third and fourth main groups, such as aluminium, tin or lead, and of the first to eight subsidiary groups, such as chromium, manganese, iron, cobalt, nickel, copper, zinc etc.. The subsidiary group elements of the 4th period are preferred. The metals may be in any one of their various valencies. The metal complexes may be mono- or polynuclear, that is to say they may contain one or more organic molecular components as ligands.

Surprisingly, however, it has been found that the combination of active ingredients I and II results in a quite unexpectedly substantial increase in activity against seed-, air- and soil-borne fungi. The increase in activity achieved by the combination according to the invention is decisively greater than the activity to be expected by adding together the activities of the two components individually.

The present invention relates not only to mixtures of components I and II, but also to the use of the individual components I and II, formulated as microbicidal compositions, in direct succession.

Favourable mixing ratios of the two active ingredients are: I:II=from 10:1 to 1:10, especially from 5:1 to 1:5, and more especially from 4:1 to 1:4. Other mixing ratios are: I:II=2:3, 1:3, 1:2, 2:5, 1:1, 5:2, 3:1, 2:1, 3:2 and 2.8:1. The mixing range I:II of from 3:1 to 3:2 is especially preferred. In this range there is an especially favourable interaction of the two active ingredients at total rates of application of from 100 to 200 g/ha.

The combination of the active components I and II according to the present invention has a beneficial systemic, protective and curative action as well as a residual action in the control of seed- and soil-borne plant diseases. The combinations according to the invention destroy microorganisms in and on the plant and protect developing plants from attack by microorganisms.

Compound I, propiconazole, is a commercially known fungicide for controlling various cereal diseases, such as Erysiphe spp., Puccinia spp., Pyrenophora spp. (=Helminthosporium spp.), Rhynchosporium spp. and others.

Compound II is a broad spectrum fungicide for controlling powdery mildew species (Erysiphe spp.), rust diseases (Puccinia spp., Hemileia etc.), leaf spot infestation (Septoria spp., Pyrenophora spp.) and others. Particularly lasting success is achieved in the control of black fungi such as Alternaria spp. and Cladosporium spp., in addition to rust and leaf spot.

The combined use of the two compounds in cereals, whether in the form of a ready-made mixture or a tank mix, provides an unexpectedly enduring increase in activity in comparison with the rates of application necessary if using the compounds individually, for example to control Septoria spp. on leaves or ears. The same applies to the prevention of attack by *Puccinia recondita*, Pyrenophora spp. and Fusarium spp. The extremely extensive prevention of these cereal diseases results in higher yields per hectare with distinctly improved crop quality.

The two-component mixture of I and II according to the invention achieves not only preventive protection, but especially also curative protection in all cases where the disease has already attacked the plant and the first signs of its spread are becoming visible. This result is observed especially in the case of rust attack (*Puccinia recondita*), which even at this stage can still be fully controlled. This advantageous property is important in all agricultural production systems that are based on forecasts of attack based upon weather, temperature and epidemics. Such a mixture provides the user with a very flexible instrument for preventing the spread of the disease even if attack has reached an advanced stage.

The mixtures of the invention are active against phytopathogenic fungi belonging to the following classes: Ascomycetes (for example the genera Mycosphaerella, Pyrenophora); Basidiomycetes (for example the genera Tilletia, Rhizoctonia); Fungi imperfecti (for example the genera Fusarium, Spetoria, Phoma, Alternaria). Other species that are difficult to control but that can be surprisingly well controlled by the mixture according to the invention are *Cercospora, Cercosporidium, Ascochyta, Ramularia, Venturia, Guignardia* and *Colletotrichum*. The combinations according to the invention are effective especially in the treatment of leaves and ears, but they are also suitable for the direct treatment of seeds or other parts of the plant (fruit, tubers, grains). They are well tolerated by plants and are ecologically harmless.

For its application, the mixture according to the invention is normally used together with adjuvants conventionally employed in the art of formulation. The active components of formulae I and II are formulated in known manner, for example, into emulsifiable concentrates, coatable pastes, directly sprayable or dilutable solutions, dilute emulsions, wettable powders, soluble powders, dusts, granulates and also encapsulations in e.g. polymer substances. The methods of application, such as spraying, atomising, dusting, scattering, coating or pouring and the form of the composition are chosen in accordance with the intended objectives and the prevailing circumstances. Favourable rates of application are generally from 50 g to 700 g of total active ingredient per hectare, the proportion of I (propiconazole) ranging from 25 g to 400 g a.i./ha and the proportion of II ranging approximately from 25 g to 300 g a.i./ha, for example from 75 to 150 g of I+40 to 125 g of II, for example I:II=125 g:50 g or I:II=75 g:75 g.

The target crops within the scope of this invention, are, for example, the following species of plants: cereals (wheat, barley, rye, oats, rice, sorghum, maize and related crops); beet (sugar beet and fodder beet); leguminous plants (beans, lentils, soybeans, peas); oil plants (rape, mustard, poppy, groundnuts, olives, sunflowers); cucumber plants (cucumbers, marrows, melons); fibre plants (cotton, flax); vegetables (cabbages, spinach, carrots, onions, garlic, tomatoes, potatoes, paprika); ornamentals (tulips, daffodils, dahlias, chrysanthemums and other flowers); tea, coffee, cocoa and mango plants, spice plants and their seeds; pomes (apples, pears), drupes (cherries, plums, peaches, nectarines); vines; turf.

A preferred method of applying the mixture of the invention comprises spraying or wetting the plant material with a liquid formulation or treating the plant material with a solid formulation of the active ingredient.

The active ingredients of formulae I and II in accordance with the invention are applied in the form of compositions and can be applied, if desired, together with further carriers, surfactants or other application-promoting adjuvants customarily employed in the art of formulation. Suitable carriers and adjuvants can be solid or liquid and correspond to the substances ordinarily employed in the art of formulation, e.g. natural or regenerated mineral substances, solvents, dispersants, wetting agents, tackifiers, thickeners, binders or fertilisers.

A preferred method of applying a mixture of active ingredients of formulae I and II or of an (agro)chemical composition containing these active ingredients, is foliar application or application to the ears, if the plant is a cereal. The number of applications and the rate of application depend on the risk of attack by the corresponding pathogen (species of fungus). The active ingredient mixture can, however, also penetrate the plant through the roots via the soil (systemic action) if the locus of the plant is impregnated with a liquid formulation, or if the substances are applied in solid form to the soil, for example in granular form (soil application). The mixture of the compounds of formulae I and II can, according to an especially preferred method, be applied (coating) to seeds, tubers, fruit or other plant material to be protected either by impregnating the material with a liquid formulation of the active ingredients or coating it with a solid formulation. In special cases, further types of application are also possible, for example selective treatment of the plant stems or buds.

The compounds of formulae I and II are used in unmodified form or, preferably, together with the adjuvants conventionally employed in the art of formulation, and are therefore formulated in known manner e.g. into emulsifiable concentrates, coatable pastes, directly sprayable or dilutable solutions, dilute emulsions, wettable powders, soluble powders, dusts, granulates, and also encapsulations in e.g. polymer substances. As with the nature of the compositions, the methods of application, such as spraying, atomising, dusting, scattering, coating or pouring, are chosen in accordance with the intended objectives and the prevailing circumstances.

The formulations, i.e. the compositions, preparations or mixtures containing the active ingredients of formulae I and II and, where appropriate, a solid or liquid adjuvant, are prepared in known manner, e.g. by homogeneously mixing and/or grinding the active ingredients with extenders, e.g. solvents, solid carriers and, where appropriate, surface-active compounds (surfactants).

Suitable solvents are: aromatic hydrocarbons, preferably the fractions containing 8 to 12 carbon atoms, e.g. xylene mixtures or substituted naphthalenes, phthalates such as dibutyl phthalate or dioctyl phthalate, aliphatic hydrocarbons such as cyclohexane or paraffins, alcohols and glycols and their ethers and esters, such as ethylene glycol monomethyl ether, ketones such as cyclohexanone, strongly polar solvents such as N-methyl-2-pyrrolidone, dimethyl sulfoxide or dimethylformamide, as well as vegetable oils or epoxidised vegetable oils, or soybean oil; or water.

The solid carriers used e.g. for dusts and dispersible powders are calcite, talcum, kaolin, montmorillonite or attapulgite, highly dispersed silicic acid or absorbent polymers. Suitable granulated adsorptive carriers are pumice, broken brick, sepiolite or bentonite; and suitable nonsorbent carriers are, for example, calcite or dolomite.

Depending on the nature of the active ingredients of formulae I and II to be formulated, suitable surface-active compounds are non-ionic, cationic and/or anionic surfactants having good emulsifying, dispersing and wetting properties. The term "surfactants" will also be understood as comprising mixtures of surfactants.

Surfactants customary in the art of formulation are described, inter alia, in the following publications:

"McCutcheon's Detergents and Emulsifiers Annual" MC Publishing Corp., Ridgewood N.J., 1980, Sisley and Wood, "Encyclopedia of Surface Active Agents", Chemical Publishing Co., Inc. New York, 1980.

The agrochemical formulations generally contain from 0.1 to 95% total active ingredient, from 99.9 to 5% of a solid or liquid adjuvant, and from 0 to 25%, especially from 0.1 to 25%, of a surfactant.

Whereas commercial products will preferably be formulated as concentrates, the end user will normally employ dilute formulations.

The present invention relates to such (agro)chemical compositions.

The following Examples serve to illustrate the invention, "active ingredient" indicating a mixture of "propiconazole" I and compound II in a particular mixing ratio ranging from 10:1 to 1:10.

| Wettable powders | a) | b) | c) |
| --- | --- | --- | --- |
| active ingredient (I:II = 10:1, 5:2, 1:3) | 25% | 50% | 75% |
| sodium lignosulfonate | 5% | 5% | — |
| sodium laurylsulfate | 3% | — | 5% |
| sodium diisobutylnaphthalene-sulfonate | — | 6% | 10% |
| octylphenol polyethylene glycol ether (7–8 moles of ethylene oxide) | — | 2% | — |
| highly dispersed silicic acid | 5% | 10% | 10% |
| kaolin | 62% | 27% | — |

The active ingredient is thoroughly mixed with the adjuvants and the mixture is thoroughly ground in a suitable mill, affording wettable powders which can be diluted with water to give suspensions of the desired concentration.

| Emulsifiable concentrate | |
| --- | --- |
| active ingredient (I:II = 4:1) | 10% |
| octylphenol polyethylene glycol ether (4–5 moles of ethylene oxide) | 3% |
| calcium dodecylbenzenesulfonate | 3% |
| castor oil polyglycol ether (35 moles of ethylene oxide) | 4% |
| cyclohexanone | 30% |
| xylene mixture | 50% |

Emulsions of any required concentration can be obtained from this concentrate by dilution with water.

| Dusts | a) | b) |
| --- | --- | --- |
| active ingredient (I:II = 3:2 and 1:1) | 5% | 8% |
| talcum | 95% | — |
| kaolin | — | 92% |

Ready-for-use dusts are obtained by mixing the active ingredient with the carrier and grinding the mixture in a suitable mill.

| Extruder granulate | |
| --- | --- |
| active ingredient (I:II = 5:2) | 10% |
| sodium lignosulfonate | 2% |
| carboxymethylcellulose | 1% |
| kaolin | 87% |

The active ingredient is mixed and ground with the adjuvants, and the mixture is subsequently moistened with water. The mixture is extruded and then dried in a stream of air.

| Coated granulate | |
| --- | --- |
| active ingredient (I:II = 3:2) | 3% |
| polyethylene glycol (MW 200) | 3% |
| kaolin | 94% |

(MW = molecular weight)

The finely ground active ingredient is uniformly applied, in a mixer, to the kaolin moistened with polyethylene glycol. Non-dusty coated granulates are obtained in this manner.

BIOLOGICAL EXAMPLES

Example 1

Action against *Puccinia graminis* on Wheat a) Residual protective action

Wheat plants are sprayed 6 days after sowing with a spray mixture (6 ppm active ingredient) prepared from a wettable powder formulation of the two active ingredients (I:II=5:2). After 24 hours, the treated plants are infected with a uredospore suspension of the fungus. The infected plants are incubated for 48 hours at 95–100% relative humidity and about 20° C. and then stood in a greenhouse at about 22° C. Evaluation of rust pustule development is made 12 days after infection.

b) Systemic action

A spray mixture (2 ppm active ingredient based on the volume of soil) prepared from a wettable powder formulation of the active ingredient is poured onto wheat plants 5 days after sowing. After 48 hours, the treated plants are infected with a uredospore suspension of the fungus. The infected plants are then incubated for 48 hours at 95–100% relative humidity and about 20° C., and then stood in a greenhouse at about 22° C. Evaluation of rust pustule development is made 12 days after infection.

The spread of the disease was prevented completely (=100% action) in both test a) and test b).

Example 2

Action against *Erysiphe graminis* on Barley a) Residual protective action

Barley plants about 8 cm in height are sprayed with a spray mixture (6 ppm active ingredient) prepared from a wettable powder formulation of the two active ingredients (I:II=3:1). The treated plants are dusted with conidia of the fungus after 3 to 4 hours. The infected barley plants are stood in a greenhouse at about 22° C. and the fungus attack is evaluated after 10 days.

b) Systemic action

A spray mixture (2 ppm active ingredient based on the volume of the soil) prepared from a wettable powder formulation of the active ingredient is poured onto barley plants about 8 cm in height. Care was taken that the spray mixture did not come into contact with the parts of the plants above the soil. The treated plants are dusted 48 hours later with conidia of the fungus. The infected barley plants are stood in a greenhouse at about 22° C. and evaluation of fungus attack is made after 10 days.

The spread of the disease had been prevented completely (=100% action) in both test a) and test b).

Example 3

Action against *Helminthosporium sativum* in Wheat

Winter wheat infected naturally with *Helminthosporium sativum* is dressed on a mixer roller with the test fungicide, a concentration of 60 ppm a.i. (based on the weight of the seeds) being applied.

The active ingredient is a 1:3 mixture of components I and II.

The infected and treated wheat is sown in October in the open with a seeder in plots 2 m long containing 3 seed rows, with 3 replicates.

The test plants are cultivated under normal field conditions until the attack is evaluated.

To determine the activity of the active ingredient, the emerged plants are evaluated. Less than 5% of the plants were infected.

Example 4

Action against Fusarium in Rye

Rye of the Tetrahell variety, naturally infected with *Fusarium nivale*, is dressed on a mixer roller with the test fungicide, the following concentrations being used: 20 or 6 ppm a.i. (based on the weight of the seeds). The a.i. is a 1:4 mixture of components I and II.

The infected and treated rye is sown in October in the open with a seeder in plots 3 m long containing 6 seed rows. 3 replicates per concentration.

The test plants are cultivated under normal field conditions (preferably in a region with unbroken snow cover during the winter months) until the attack is evaluated.

In order to evaluate the phytotoxicity, in autumn the seed emergence and in spring the crop density/number of plants per unit area is evaluated.

To determine the active ingredient activity, the percentage number of plants attacked by Fusarium is counted in the spring, directly after the snow has melted. The number of infected plants in the present case was less than 5%. The emerged plants had a healthy appearance.

Example 5

Action against *Septoria nodorum* on Wheat

Wheat plants are sprayed at the 3-leaf stage with a spray mixture (60 ppm a.i.) prepared from a wettable powder formulation of the active ingredients (2.8:1).

24 hours later, the treated plants are infected with a conidia suspension of the fungus. The plants are then incubated for 2 days at 90-100% relative humidity and stood in a greenhouse for a further 10 days at 20°-24° C. The fungus attack is assessed 13 days after infection. Less than 1% of the wheat plants exhibited any attack.

What is claimed is:

1. A plant fungicidal composition containing a plant synergistic fungicidally effective amount of a plant fungicidally active ingredient, said active ingredient essentially consisting of a mixture of two active ingredient components I) and II), component I) being 1-[2-(2,4-dichloro-phenyl)-4-propyl-1,3-dioxolan-2-ylmethyl]-1H-1,2,4-triazole of the formula

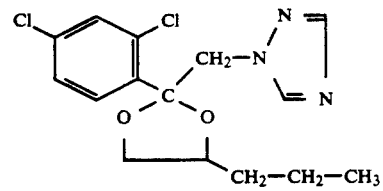

or a salt thereof and component II) being 1-{2-[2-chloro-4-(4-chlorophenoxy)-phenyl]-4-methyl-1,3-dioxolan-2-ylmethyl}-1H-1,2,4-triazole of the formula

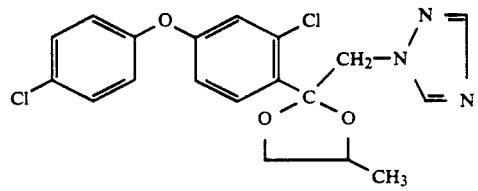

or a salt thereof, together with a suitable carrier, the synergistic ratio by weight of I):II) being from 10:1 to 1:10.

2. A composition according to claim 1, wherein the ratio by weight of I):II) is from 5:1 to 1:5.

3. A composition according to claim 2, wherein the ratio by weight of I):II) is from 4:1 to 1:4.

4. A composition according to claim 3, wherein the ratio by weight of I):II) is from 3:1 to 3:2.

5. A method of controlling or preventing plant fungal diseases, which comprises treating the plant, which is already infected or is liable to be infected, or the locus of said plant, with a synergistic fungicidally effective amount of the composition according to claim 1.

6. A method according to claim 4, wherein cereals are treated.

7. A method according to claim 5, wherein vegetables, potatoes or sugar beets are treated.

8. A method according to claim 5 for controlling or preventing Fusarium spp., Puccinia spp., Pyrenophora spp. or Septoria spp fungi.

9. A method according to claim 5, wherein 50 g to 700 g of active ingredient are applied per hectare.

* * * * *